United States Patent [19]

D'Silva

[11] 4,382,957

[45] May 10, 1983

[54] SYMMETRICAL INSECTICIDAL BIS-CARBAMATE COMPOUNDS

[75] Inventor: Themistocles D. J. D'Silva, South Charleston, W. Va.

[73] Assignee: Union Carbide Corporation, Danbury, Conn.

[21] Appl. No.: 636,373

[22] Filed: Dec. 1, 1975

[51] Int. Cl.³ .................... A01N 33/24; A01N 33/26
[52] U.S. Cl. ............................... 424/327; 260/453.3; 260/465.4; 424/270; 424/276; 424/277; 424/298; 424/300; 424/304; 548/185; 549/30; 549/38; 564/101
[58] Field of Search ............... 424/298, 300, 327, 304, 424/270, 276, 277; 260/453 R, 479, 453.3, 465.4; 548/185; 549/30, 38; 564/101

[56] References Cited

U.S. PATENT DOCUMENTS 3,679,733 7/1972 Brown et al. .................. 424/300
3,794,733 2/1974 Brown et al. .................. 424/300
3,920,830 11/1975 Brown et al. .................. 424/300

FOREIGN PATENT DOCUMENTS 831212 7/1975 Belgium .

OTHER PUBLICATIONS

Fahmy et al., J. Agr. Food Chem., vol. 22 (1974), pp. 59–62.

Primary Examiner—Leonard Schenkman
Attorney, Agent, or Firm—Robert C. Brown

[57] ABSTRACT

Symmetrical N-substituted bis-carbamoyl sulfide compounds exhibit exceptional broad spectrum pesticidal activity coupled with extremely low mammalian toxicity and phytotoxicity.

40 Claims, No Drawings

SYMMETRICAL INSECTICIDAL BIS-CARBAMATE COMPOUNDS

This invention relates to methods and compositions for controlling insect, acarid and nematode pests. In another aspect this invention relates to novel symmetrical N-substituted bis-carbamoyl sulfide compounds and to their production.

The compounds which are employed as the active ingredients in the pesticidal compositions of this invention are symmetrical bis-carbamoyl sulfide compounds of the following general formula:

$$RO-\underset{\underset{O}{\|}}{C}-\underset{\underset{R'}{|}}{N}-S-\underset{\underset{R'}{|}}{N}-\underset{\underset{O}{\|}}{C}-OR$$

wherein:
R is:

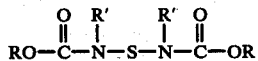

wherein:
$R_2$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or $R_4R_5$—NCO— groups; or $R_2$ is phenyl, $R_4R_5$NCO— or $R_6CON(R_4)$—;
wherein:
$R_4$ and $R_5$ are individually hydrogen or alkyl;
$R_6$ is hydrogen, alkyl or alkoxy; $R_3$ is hydrogen, alkyl, alkylthio or cyano;
A is a four or five member divalent aliphatic chain which includes one or two divalent oxygen, sulfur, sulfenyl or sulfonyl groups and which may include not more than one divalent amino, alkylamino or carbonyl groups, in any combination;
provided that the total number of carbon atoms in R may not exceed eight and provided further that when $R_2$ is alkyl substituted with alkylthio, $R_3$ is cyano alkyl or alkylthio; and
R' is alkyl containing from one to four carbon atoms.

The preferred compounds of this invention are those in which R' is methyl. The active compounds of this invention exhibit a very high level of pesticidal activity coupled with a substantially reduced mammalian toxicity and phytotoxicity as compared with other known pesticidal compounds having a comparable spectrum of activity against insect, nematode and arachnid pests. It has been found however that while compounds according to the above formula, wherein $R_2$ is an alkylthioalkyl substituent and $R_3$ is hydrogen, exhibit good pesticidal activity, their mammalian toxicity is unacceptably high in relation to the properties of compounds falling within the scope of the above generic formula.

The symmetrical bis-carbamoyl sulfides of this invention can be prepared conveniently by the method shown in the following general reaction scheme:

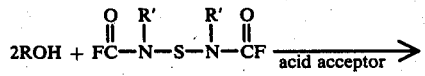 $\xrightarrow{\text{acid acceptor}}$ (I)

wherein R and R' are as defined above.

Two equivalents of the oxime reactant (ROH) are reacted with the bis-carbamoyl fluoride in the presence of two equivalents of an acid acceptor, preferably in an inert solvent. The acid acceptor employed can be either an organic or inorganic base such as triethylamine or sodium or potassium hydroxide. A phase transfer agent such as a crown ether may also be employed. Any conventional inert solvent can be used, such as benzene, toluene, dioxane, tetrahydrofuran, ethylether, methylene chloride or the like.

This reaction may also be carried out in a two phase system using an aqueous solution of an inorganic base as one phase and an aromatic solvent including a quaternary ammonium salt as a phase transfer agent as the second phase. The reaction temperature is not critical. The reaction goes essentially to completion at room temperature. Elevated temperatures may be employed if it is desired to reduce reaction time.

An alternative method of preparing the symmetrical bis-carbamoyl sulfide compounds of this invention is illustrated by the following general reaction scheme:

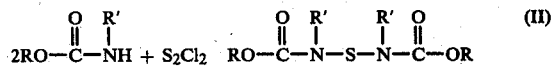 (II)

In this procedure two equivalents of a carbamate compound are reacted with sulfur monochloride in the presence of two equivalents of an acid acceptor such as pyridine, preferably in an inert solvent to produce the symmetrical bis-carbamoyl sulfides of this invention. The carbamate compounds employed in this procedure are known compounds which are generally prepared by reacting the corresponding oxime compounds with an alkylisocyanate compound.

The oxime reactants (ROH) employed in the reactions described above are known compounds which can be prepared by conventional methods. See for example U.S. Pat. Nos. 3,752,841, 3,726,908, 3,843,669; and Belgian Pat. Nos. 813,206 and 815,513.

The following compounds are illustrative of the new compounds of this invention:
N,N'-bis-[1-methylthioacetaldehyde O-(N-methylcarbamoyl)oxime sulfide, alternatively known as bis-[O-(1-methylthioethylimino)-N-methylcarbamic acid]-N,N'-sulphide.
N,N'-[1-Ethylthioacetaldehyde O-(N-methylcarbamoyl)oxime]sulfide.
N,N'-bis-[1-Isopropylthioacetaldehyde O-(N-methylcarbamoyl)oxime]sulfide.
N,N'-bis-[1-(2-cyanoethylthio)acetaldehyde O-(N-methylcarbamoyl)oxime]sulfide.
N,N'-bis-[5-Methyl-4-(O-(N-methylcarbamoyl)oximino)-1,3-oxathiolane]sulfide.
N,N'-bis-[2-(O-(N-methylcarbamoyl)oximino)-1,4-dithiane]sulfide.
N,N'-bis-[4-(O-(N-methylcarbamoyl)oximino)1,3-dithiolane]sulfide.
N,N'-bis-[5,5-dimethyl-4-(O-(N-methylcarbamoyl)oximino)1,3-dithiolane]sulfide,
N,N'-bis-[3,5,5-trimethyl-2-(O-N-methylcarbamoyl)-oximino)thiazolidin-4-one]sulfide.

N,N'-bis-[4,5,5-trimethyl-2-(O-(N-methylcarbamoyl)-
oximino)thiazolidin-3-one]sulfide.

N,N'-bis-[2-(O-(N-methylcarbamoyl)oximino)-1,3-
dithiolane]sulfide.

N,N'-bis-[2-cyano-2-methylpropionaldehyde O-(N-methylcarbamoyl)oxime]sulfide.

N,N'-bis-[2-nitro-2-methylpropionaldehyde O-(N-methylcarbamoyl)oxime]sulfide.

N,N'-bis-[1-Methylthio-N",N'''-dimethylcarbamoylformaldehyde O-(N-methylcarbamoyl)oxime]sulfide.

N,N'-bis-[4-methyl-2-(O-(N-methylcarbamoyl)oximino)-tetrahydro-1,4-thiazin-3-one]sulfide.

N,N'-bis-[3,3-Dimethyl-1-methylthiobutanone-2 O-(N-methylcarbamoyl)oxime]sulfide.

N,N'-bis-[3-Methylthiobutanone-2 O-(N-methylcarbamoyl)oxime]sulfide.

N,N'-bis-[3-Methylsulfonylbutanone-2 O-(N-methylcarbamoyl)oxime]sulfide.

N,N'-bis-[2-Methylsulfonyl-2-methylpropionaldehyde O-(N-methylcarbamoyl)oxime]sulfide.

N,N'-bis-[1-Methylthiopyruvaldehyde O-(N-methylcarbamoyl)oxime]sulfide.

N,N'-bis-[3,3-Dimethyl-1-methylsulfonylbutanone-2 O-(N-methylcarbamoyl)oxime]sulfide.

N,N'-bis-1-[N-(Dimethylaminomethylene)carbamoyl]-1-methylthioformaldehyde O-(N-methylcarbamoyl)oxime]sulfide.

N,N'-bis-[1-Methylthio-1-ethoxycarbonylformaldehyde O-(N-methylcarbamoyl)oxime]sulfide.

N,N'-bis-[1,3,5-Oxadithiane-4 O-(N-methylcarbamoyloximino)]sulfide.

N,N'-bis-[1,3,5-Trithiane-2 O-(N-methylcarbamoyloximino)]sulfide.

N,N'-bis-3-[O-(N-methylcarbamoyl)oximino-1,4-oxathiane]sulfide.

N,N'-bis-[1-cyano-2,2-dimethylpropionaldehyde O-(N-methylcarbamoyloxime)]sulfide.

N,N'-bis-[4-methyl-2-(O-(N-methylcarbamoyl)oximino-tetrahydro-1,4-thiazin-5-one]sulfide.

The following examples are provided to illustrate the procedures used for the preparation of the compounds of this invention.

EXAMPLE I

Preparation of Bis-(N-Methyl-N-fluorocarbonylamino)sulfide

To a polypropylene reactor containing 80 g (4.0 m) of hydrogen fluoride in 1800 ml of toluene, cooled to −40° C. was added dropwise with stirring 228 g (4.0 m) of methylisocyanate, over a period of 20 min. The reaction mixture was allowed to warm to 0° C. and was maintained at this temperature for 1 hr. Then 60 g (2 m) of freshly distilled sulfur dichloride was added followed by a slow addition of 346 g (4.4 m) of pyridine at −20° to −0° C. After stirring for 2 hrs. at −10° C. and for 16 hrs. at ambient temperature, the reaction mixture was diluted with 500 ml of water. The toluene layer was further washed with (3×500 ml) water dried and distilled to yield 244 g (66 percent) of the product. B.P. 55°–57° C./0.25 mm. m.p. 40°–41° C.

Calc'd for $C_4H_6F_2N_2O_2S$: C, 26.09; H, 3.28; N, 15.21; Found: C, 26.19; H, 3.20; N, 14.79.

EXAMPLE II

Preparation of N,N'-bis-[1-Methylthioacetaldehyde O-(N-methylcarbamoyl)oxime]sulfide (Method I)

Procedure A

To a solution of 0.50 g of bis-(N-methyl-N-fluorocarbonylamino)sulfide and 0.526 g of 1-methylthioacetaldoxime in 15 ml dioxane was added 0.505 g of triethylamine. After stirring for 20 hrs. at room temperature, the reaction mixture was diluted with water. The N,N'-bis[1-methylthioacetaldehyde O-(N-methylcarbamoyl)oxime]sulfide solid was filtered and taken in methylene chloride. The organic extract was washed with water, dried and concentrated. Weight of product 0.60 g. m.p. 173°–174° C.

Calc'd. for $C_{10}H_{18}N_4O_4S_3$: C, 33.88; H, 5.12; N, 15.81; Found: C, 33.72; H, 5.15; N, 15.49

EXAMPLE III

Preparation of N,N'-bis-[1-Methylthioacetaldehyde O-(N-methylcarbamoyl)oxime]sulfide (Method I)

Procedure B

To a solution of 36.9 g of bis-(N-methyl-N-fluorocarbonylamino)sulfide and 42.0 g of 1-methylthioacetaldoxime in 500 ml of toluene was added 40.47 g of triethylamine. The spontaneous exotherm raised the temperature to 32° C. After stirring for 16 hrs. at ambient temperature an additional 100 ml of toluene was added and the reaction mixture heated to about 45° C. for 2 hrs. It was then cooled to 10° C. and filtered. The solid was washed with water and rinsed with isopropanol and air dried to yield 54.46 g of white solid N,N'-bis[1-methylthioacetaldehyde O-(N-methylcarbamoyl)oximino]sulfide m.p. 170°–173° C. recrystallized from methylene chloride m.p. 173°–174° C.

EXAMPLE IV

Preparation of N,N'-bis-[1-Methylthioacetaldehyde O-(N-methylcarbamoyl)oxime]sulfide (Method II)

To a solution of 1.62 g of 1-methylthioacetaldehyde O-(N-methylcarbamoyl)oxime and 0.67 g of sulfur monochloride in 25 ml of toluene was added 0.79 g of pyridine. After stirring for 16 hrs. the solid was filtered off, was washed with water and dried to yield 0.7 g of the N,N'-bis-[1-methylthioacetaldehyde O-(n-methylcarbamoyl)oxime]sulfide m.p. 174°–178° C. (identical by tlc and nmr to the product obtained in Examples II and III.

EXAMPLE V

Preparation of N,N'-bis-[1-(2-cyanoethylthio)acetaldehyde O-(N-methylcarbamoyl)oxime]sulfide To a suspension of 14.4 g of 1-(2-cyanoethylthio)acetaldoxime and 8.63 g of bis-(N-methyl-N-fluorocarbonylamino)sulfide in 70 ml of toluene was added dropwise 10.1 g of triethylamine diluted with 10 ml of toluene. The temperature of the reaction was maintained under 30°. After stirring for 20 hrs. at room temperature the solid suspension was filtered and washed with 10 percent isopropanol in water. The filtrate was discarded and the solid N,N'-bis-[1-(2-cyanoethylthio)acetaldehyde O-(N-methylcarbamoyl)oxime]sulfide (10.0 g) was crystallized from acetonitrile-methylene chloride. m.p. 189°–190° C.

Calc'd for $C_{14}H_{20}N_6O_4S_3$: C, 38.87; H, 4.66; N, 19.43. Found: C, 38.50; H, 4.61; N, 19.11.

EXAMPLE VI

Preparation of N,N'-bis-[2-Methylsulfonyl-2-methylpropionaldehyde O-(N-methylcarbamoyl)oxime]sulfide To a solution of 4.0 g of 2-methylsulfonyl-2-methylpropionaldoxime and 2.1 g of bis-(N-methyl-N-fluorocarbonylamino)sulfide in 50 ml of toluene was added 2.45 g of triethylamine diluted with 25 ml of toluene. The reaction mixture was allowed to stand at ambient temperature for 62 hours. The precipitated solid was removed by filtration, was dissolved in methylene chloride, washed with water and dried over magnesium sulfate. On concentration and recrystallization from ethyl acetate it yielded 2.9 g of N,N'-bis-[2-methylsulfonyl-2-methylpropionaldehyde O-(N-methylcarbamoyl)oxime]sulfide in the form of a white solid. m.p. 124°–125° C.

Calc'd for $C_{14}H_{26}N_4O_8S_3$: C, 35.43; H, 5.52; N, 11.81; Found: C, 35.38; H, 5.56; N, 11.57

EXAMPLE VII

Preparation of N,N'-bis-[2-Cyano-2-methylpropionaldehyde O-(N-methylcarbamoyl)oxime]sulfide To a solution of 4.48 g of 2-cyano-2-methylpropionaldoxime and 3.37 g of bis-(N-methyl-N-fluorocarbonylamino)sulfide in 75 ml of toluene was added 4.04 g of triethylamine diluted with 25 ml of toluene. After stirring for 2 hrs. an additional 0.63 g of bis-(N-methyl-N-fluorocarbonyl)amino sulfide was added and the reaction mixture heated at 30°–40° C. for 2.5 hrs. The solvent was removed under reduced pressure and the residue was dissolved in ethylacetate and water. The organic layer was washed with water, dried over magnesium sulfate and concentrated under reduced pressure. The product, N,N'-bis-[2-cyano-2-methylpropionaldehyde O-(N-methylcarbamoyl)oxime]sulfide was crystallized from isopropylether-ethyl acetate. Weight of product 1.32 g m.p. 110°–112° C.

Calc'd for $C_{14}H_{20}N_6O_4S$: C, 45.64; H, 5.46; N, 22.81; Found: C, 45.49; H, 5.49; N, 22.44

EXAMPLE VIII

Preparation of N,N'-bis-[1-Methylthio-1-(N'',N''-dimethylcarbamoyl)-formaldehyde O-(N-methylcarbamoyl)oxime]sulfide To a solution of 3.24 g of 1-methylthio-N,N-dimethylcarbamoyl formaldoxime and 2.0 g of bis-(N-methyl-N-fluorocarbonylamino)sulfide in 100 ml of toluene was added 2.02 g of triethylamine. After stirring for 20 hrs. the reaction mixture was washed with water. The toluene solution was dried over magnesium sulfate and concentrated to yield a solid residue. Crystallization from ethylacetate yielded 2.1 g of white solid N,N'-bis-[1-methylthio-1-(N'',N''-dimethylcarbamoyl)formaldehyde O-(N-methylcarbamoyl)oxime]sulfide. m.p. 190°–192° C.

Calc'd for $C_{14}H_{24}N_6O_6S_3$: C, 35.88; H, 5.16; N, 17.9; Found: C, 35.75; H, 5.56; N, 17.5

EXAMPLE IX

Preparation of N,N-bis-[1,4-Dithiane-2-O-(N-methylcarbamoyl)oxime]sulfide

Prepared by the procedure employed in Example VIII by reacting 5.0 of 2-oximino-1,4-dithiane with 2.89 g of bis-(N-methyl-N-fluorocarbonylamino)sulfide and 3.39 g of triethylamine. Weight of the product N,N'-bis-[1,4-dithiane-2-O-(N-methylcarbamoyl)oximino]sulfide 4.7 g. m.p. 209°–211° C.

Calc'd. for $C_{12}H_{18}N_4O_4S_5$: C, 32.56; H, 4.10; N, 12.66; Found: C, 32.10; H, 3.87; N, 12.21

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50± percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation.

Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243-244, 261) under controlled conditions of 80°± F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stage of the two-spotted mite (*Tetranychus urticae Koch*), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Nematocide Test

The test organism used was the infective migratory larvae of the root-knot nematode, *Meloidogyne incognita* var. *acrita*, reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots; and the amount of galling visually rated.

The results of these tests are set forth in Table I below. In these tests the pesticidal activity of the compounds at the indicated dosage rate against aphid, mite, Southern Armyworm, Bean Beetle and house fly was rated as follows:

A=excellent control
B=partial control
C=no control

In the test for activity against nematodes activity was rated as follows:

1=severe galling, equal to untreated plants
2=moderate galling
3=light galling
4=very light galling
5=no galling, perfect control Dashes indicate no test conducted.

Phytotoxicity Test

Experiments were also conducted to determine the phytotoxicity of representative compounds with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the foliage to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

Mammalian Toxicity

Certain compounds were also evaluated to determine their peroral toxicity to mammals by conventional methods. The representative animal selected for this experiment was the rat. The test results obtained are expressed in terms of the number of milligrams of composition per kilogram of weight of the animal required to achieve a mortality rate of 50 percent ($LD_{50}$).

The results of these experiments are also summarized in Table I below.

TABLE I

| Compound | (Ex.) m.p. °C. | Biological Activity | | | | | | A.O. Rat Mg/Kg. | Phytotoxicity | | | | |
|---|---|---|---|---|---|---|---|---|---|---|---|---|---|
| | | Aphid | Mite | S.A. | M.B.B. | Fly | Nem. | | Bean | Corn | Tom. | Cotton | Soy |
| $CH_3C=NOC-N-S-N-CON=CCH_3$ with $O$, $CH_3$, $CH_3$, $O$ groups and $SCH_3$, $SCH_3$ | (II) 173–74 | A | A | A | A | A | 5 | 160.0 | 1 | 1 | 1 | 1 | 1 |
| (structure with $CH_3$, $O$, $S$ ring, $NOC-N-S-N$ linkage) | 146–48 | A | A | A | A | A | — | 15.9 | 1 | 1 | 1 | 1 | 1 |
| (cyclic structure with $CH_3$, $N$, $S$, $C(CH_3)_2$, C=O) | 227–30 | C | C | A | A | C | 1 | — | 1 | 1 | 1 | 1 | 1 |
| $CH_3C=NOC-N-S-N-CON=CCH_3$ with $SCH_2CH_2CN$ and $NCCH_2CH_2S$ | (V) 189–90 | B | A | A | A | A | 3 | 56.6 | 1 | 1 | 1 | 1 | 1 |
| $CH_3C=NOC-N-S-N-CON=CCH_3$ with $SCH(CH_3)_2$ and $(CH_3)_2CHS$ | 115–16 | A | A | A | A | A | 4 | 40.0 | 1 | 1 | 1 | 1 | 2 |
| structure with $CH_3NC-C=NOC-N-S-N-CON=C-CN$ and $SCH_3$, $CH_3$ | (VIII) 190–92 | A | A | C | A | A | 5 | 7.07 | 1 | 1 | 1 | 1 | 1 |
| $C_2H_5OCC=NOC-N-S-N-CON=CCOC_2H_5$ with $SCH_3$, $CH_3$, $SCH_3$ | 93–94 | A | C | B | A | B | 4 | — | 1 | 1 | 1 | 1 | 1 |

TABLE I-continued

| Compound | (Ex.) m.p. °C. | Biological Activity | | | | | | | A.O. Rat Mg/Kg. | Phytotoxicity | | | | |
|---|---|---|---|---|---|---|---|---|---|---|---|---|---|---|
| | | Aphid | Mite | S.A. | M.B.B. | Fly | Nem. | | | Bean | Corn | Tom. | Cotton | Soy |
| ![structure] O CH₃ CH₃ O ‖ ‖ NOC—N—S—N—CON= with thiolane rings | 130-35 | C | C | C | C | A | 4 | — | | 1 | 1 | 1 | 1 | 1 |
| ![structure] OCH₃ CH₃ O S \ ‖ ‖ ∥ =NOCN—S—N—C—O—N= with dithiolane rings | 187-189 | | | | | | | | | | | | | |
| ![structure] O CH₃ CH₃ O ‖ ‖ NOC—N—S—N—CON= with 1,3-dithiane rings | (IX) 209-11 | C | A | C | A | A | 4 | >640.0 | | 1 | 1 | 1 | 2 | 2 |
| CH₃S—CCH=CNOC—N—S—N—CON=CHC—SCH₃ with O=S=O, CH₃ groups | (VI) 124-25 | C | A | C | A | A | 4 | 28.3 | | 1 | 1 | 1 | 1 | 4 |
| CH₃ O CH₃ CH₃ O  NCCCH=NOC—N—S—N—CON=CHCCN  CH₃  CH₃ | (VII) 110-12 | A | A | A | A | A | 1 | 10.0 | | 2 | 1 | 2 | 1 | 2 |

It will be understood that the insect species and other pests employed in the above tests are merely representative of a wide variety of pests that can be controlled by use of the novel compounds of this invention.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attach by insects, mites and nematodes upon plants or other material to which the pesticides are applied. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as well as combinations of the active compounds of this invention with other biologically active compounds.

What is claimed is:

1. A compound of the formula:

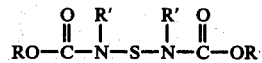

wherein:
R is:

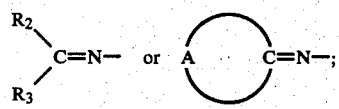

wherein:
$R_2$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or $R_4R_5$—NCO— groups; or $R_2$ is phenyl, $R_4R_5$NCO— or $R_6$CON($R_4$)—;
wherein:
$R_4$ and $R_5$ are individually hydrogen or alkyl;
$R_6$ is hydrogen, alkyl or alkoxy;
$R_3$ is hydrogen, alkyl, alkylthio or cyano;
A is a four or five member divalent aliphatic chain which includes one or two divalent oxygen, sulfur, sulfinyl or sulfonyl groups and which may include not more than one divalent amino, alkylamino or carbonyl groups, in any combination;
provided that the total number of carbon atoms in R may not exceed eight and provided further that when $R_2$ is alkyl substituted with alkylthio, $R_3$ is alkyl or alkylthio; and
R' is alkyl containing from one to four carbon atoms.

2. A compound of the formula:

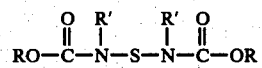

wherein:
R is:

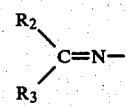

wherein:
$R_2$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or $R_4R_5$—NCO— groups; or $R_2$ is phenyl, $R_4R_5$NCO— or $R_6$CON($R_4$)—;
wherein:
$R_4$ and $R_5$ are individually hydrogen or alkyl;
$R_6$ is hydrogen, alkyl or alkoxy;
$R_3$ is hydrogen, alkyl, alkylthio or cyano; provided that the total number of carbon atoms in R may not exceed eight and provided further than when $R_2$ is alkyl substituted with alkylthio, $R_3$ is alkyl or alkylthio; and
R' is alkyl containing from one to four carbon atoms.

3. A compound according to claim 2 wherein R' is methyl.

4. A compound according to claim 2 wherein $R_3$ is alkyl.

5. A compound according to claim 2 wherein $R_3$ is alkylthio.

6. N,N'-bis[1-(2-cyanoethylthio)acetaldehyde O-(N-methylcarbamoyl)oximino]sulfide.

7. N,N'-bis[1-Isopropylthioacetaldehyde O-(N-methylcarbamoyl)oxime]sulfide.

8. N,N'-bis[2-Methylsulfonyl-2-methylpropionaldehyde O-(N-methylcarbamoyl)oxime]sulfide.

9. A compound of the formula I

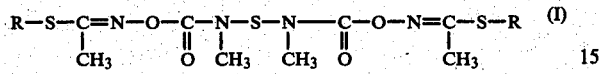

wherein R represents a $C_1$–$C_5$-alkyl radical.

10. A compound according to claim 9 wherein R represents a methyl, ethyl, n-propyl, isopropyl, n-butyl or i-butyl radical.

11. Bis-[O-(1-methylthioethylimino)-N-methylcarbamic acid]-N,N'-sulphide according to claim 10.

12. A pesticidal composition comprising an insecticidally or miticidally effective amount of at least one compound of the formula:

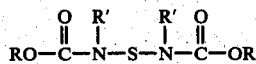

wherein:
R is:

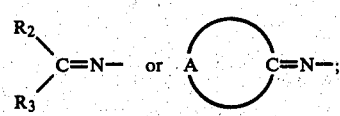

wherein:
$R_2$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or $R_4R_5$—NCO—groups; or $R_2$ is phenyl, $R_4R_5NCO$— or $R_6CON(R_4)$—;
wherein:
$R_4$ and $R_5$ are individually hydrogen or alkyl;
$R_6$ is hydrogen, alkyl or alkoxy;
$R_3$ is hydrogen, alkyl, alkylthio or cyano;
A is a four or five member divalent aliphatic chain which includes one or two divalent oxygen, sulfur, sulfinyl or sulfonyl groups and which may include not more than one divalent amino, alkylamino or carbonyl groups, in any combination;
provided that the total number of carbon atoms in R may not exceed eight and provided further that when $R_2$ is alkyl substituted with alkylthio, $R_3$ is alkyl or alkylthio; and
R' is alkyl containing from one to four carbon atoms; and an acceptable carrier.

13. A composition according to claim 12 wherein R is:

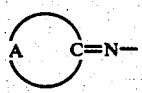

14. A composition according to claim 12 wherein R is:

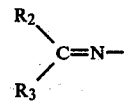

15. A pesticidal composition comprising an insecticidally or miticidally effective amount of at least one compound of the formula:

wherein:
R is:

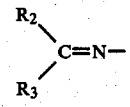

wherein:
$R_2$ is alkyl, alkylthio, alkoxy, ankanoyl or alkoxycarbonyl, all of which may be unsubstituted or aliphatically substituted in any combination with one or more cyano, nitro, alkylthio, alkylsulfonyl, alkylsulfonyl, alkoxy or $R_4R_5$—NCO— groups; or $R_2$ is phenyl, $R_4R_5NCO$— or $R_6CON(R_4)$—;
wherein:
$R_4$ and $R_5$ are individually hydrogen or alkyl;
$R_6$ is hydrogen, alkyl or alkoxy;
$R_3$ is hydrogen, alkyl, alkylthio or cyano;
provided that the total number of carbon atoms in R may not exceed eight and provided further than when $R_2$ is alkyl substituted with alkylthio, $R_3$ is alkyl or alkylthio; and
R' is alkyl containing from one to four carbon atoms; and an acceptable carrier.

16. A composition according to claim 15 wherein R' is methyl.

17. A composition according to claim 15 wherein $R_3$ is alkyl.

18. A composition according to claim 15 wherein $R_3$ is alkylthio.

19. A composition according to claim 15 wherein said compound is N,N'-bis-[1-methylthioacetaldehyde O-(N-methylcarbamoyl)oxime]sulfide.

20. A composition according to claim 15 wherein said compound is N,N'-bis-[1-(2-cyanoethylthio)acetaldehyde O-(N-methylcarbamoyl)oxime]sulfide.

21. A composition according to claim 15 wherein said compound is N,N'-bis-[1-Isopropylthioacetaldehyde O-(N-methylcarbamoyl)oxime]sulfide.

22. A composition according to claim 15 wherein said compound is N,N'-bis-[2-Methylsulfonyl-2-methylpropionaldehyde O-(N-methylcarbamoyl)oxime]sulfide.

23. An insecticidal composition comprising an insecticidally effective amount of a compound according to claim 9, together with a suitable carrier therefor.

24. The composition of claim 23, wherein in said compound R represents a methyl, ethyl, n-propyl, isopropyl, n-butyl or i-butyl radial.

25. The composition of claim 24, wherein said compound is bis-[O-(1-methylthioethylimino)-N-methylcarbamic acid]-N,N'-sulphide.

26. A method of controlling insects and mites which comprises subjecting them to an insecticidally or miticidally effective amount of a compound of the formula:

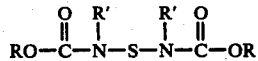

wherein:
R is:

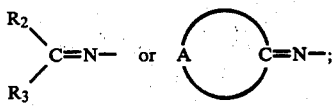

wherein:
R$_2$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or R$_4$R$_5$—NCO—groups; or R$_2$ is phenyl, R$_4$R$_5$NCO— or R$_6$CON(R$_4$)—;
wherein:
R$_4$ and R$_5$ are individually hydrogen or alkyl;
R$_6$ is hydrogen, alkyl or alkoxy;
R$_3$ is hydrogen, alkyl, alkylthio or cyano;
A is a four or five member divalent aliphatic chain which includes one or two divalent oxygen, sulfur, sulfinyl or sulfonyl groups and which may include not more than one divalent amino, alkylamino or carbonyl groups, in any combination;
provided that the total number of carbon atoms in R may not exceed eight and provided further that when R$_2$ is alkyl substituted with alkylthio, R$_3$ is alkyl or alkylthio; and
R' is alkyl containing from one to four carbon atoms.

27. A method according to claim 26 wherein R is:

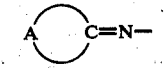

28. A method according to claim 26 wherein R is:

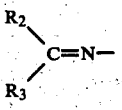

29. A method of controlling insects and mites which comprises subjecting them to an insecticidally or miticidally effective amount of a compound of the formula:

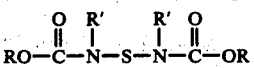

wherein:
R is:

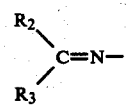

wherein:
R$_2$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or R$_4$R$_5$—NCO— groups; or R$_2$ is phenyl, R$_4$R$_5$NCO— or R$_6$CON(R$_4$)—;
wherein:
R$_4$ and R$_5$ are individually hydrogen or alkyl;
R$_6$ is hydrogen, alkyl or alkoxy;
R$_3$ is hydrogen, alkyl, alkylthio or cyano;
provided that the total number of carbon atoms in R may not exceed eight and provided further than when R$_2$ is alkyl substituted with alkylthio, R$_3$ is alkyl or alkylthio; and
R' is alkyl containing from one to four carbon atoms.

30. A method according to claim 29 wherein R' is methyl.

31. A method according to claim 29 wherein R$_3$ is alkyl.

32. A method according to claim 29 wherein R$_3$ is alkylthio.

33. A method according to claim 29 wherein said compound is N,N'-bis-[1-methylthioacetaldehyde O-(N-methylcarbamoyl)oxime]sulfide.

34. A method according to claim 29 wherein said compound is N,N'-bis-[1-(2-cyanoethylthio)acetaldehyde O-(N-methylcarbamoyl)oxime]sulfide.

35. A method according to claim 29 wherein said compound is N,N'-bis-[1-Isopropylthioacetaldehyde O-(N-methylcarbamoyl)oxime]sulfide.

36. A method according to claim 29 wherein said compound is N,N'-bis-[2-Methylsulfonyl-2-methylpropionaldehyde O-(N-methylcarbamoyl)oxime]sulfide.

37. A method for combatting insects which comprises applying to the locus of said insects an insecticidally effective amount of a compound according to claim 9.

38. The method of claim 37, wherein said locus is cotton plants.

39. The method of claim 37, wherein in said compound R represents a methyl, ethyl, n-propyl, isopropyl, n-butyl or i-butyl radical.

40. The method of claim 39, wherein said compound is bis-[O-(1-methylthioethylimino)-N-methyl-carbamic acid]-N,N'-sulphide.

* * * * *